United States Patent
Bobulski

(10) Patent No.: US 6,439,053 B1
(45) Date of Patent: Aug. 27, 2002

(54) ACOUSTIC SPECTROMETER APPARATUS AND METHOD FOR CAVITY GEOMETRY VERIFICATION

(76) Inventor: Henry Alan Bobulski, 3545 Makassar Dr., Westerville, OH (US) 43081

( * ) Notice: Subject to any disclaimer, the term of this patent is extended or adjusted under 35 U.S.C. 154(b) by 85 days.

(21) Appl. No.: 09/660,608

(22) Filed: Sep. 13, 2000

(51) Int. Cl.$^7$ .............................................. G01N 29/04
(52) U.S. Cl. .......................... 73/579; 73/592; 73/600; 73/602; 73/659
(58) Field of Search .................... 73/579, 600, 602, 73/657, 659, 40, 40.5 A, 45.4, 47, 49.5, 52, 592

(56) References Cited

U.S. PATENT DOCUMENTS

| | | | | |
|---|---|---|---|---|
| 3,584,504 A | * | 6/1971 | Proctor | 73/67.8 |
| 4,117,731 A | * | 10/1978 | Heyman | 73/579 |
| 4,480,473 A | * | 11/1984 | Varterasian | 73/596 |
| 5,060,507 A | * | 10/1991 | Urmson et al. | 73/24.01 |
| 5,062,296 A | * | 11/1991 | Migliori | 73/579 |
| 5,088,327 A | * | 2/1992 | Gammell | 73/588 |
| 5,109,699 A | * | 5/1992 | Voruz | 73/592 |
| 5,408,880 A | * | 4/1995 | Rhodes et al. | 73/579 |
| 5,861,547 A | * | 1/1999 | Kawai et al. | 73/49.2 |
| 6,212,942 B1 | * | 4/2001 | Hara et al. | 73/40.5 A |
| 6,286,370 B1 | * | 9/2001 | Sinha | 73/579 |

* cited by examiner

Primary Examiner—Herzon Williams
Assistant Examiner—Jacques Saint-Surin
(74) Attorney, Agent, or Firm—David G. Herold

(57) ABSTRACT

The geometry of a cavity in a cast, molded or machined part is compared to that of a reference part. Measuring the amplitude or phase shift of an acoustic wave traveling through the sealed cavity, at a multiplicity of predetermined frequencies, forms an acoustic spectrum, unique to the geometry of the cavity. The acoustic spectrum of the part under test is compared to the acoustic spectrum obtained from the corresponding cavity in a reference part.

18 Claims, 8 Drawing Sheets

ACOUSTIC SPECTROMETER APPARATUS AND METHOD FOR CAVITY GEOMETRY VERIFICATION

BACKGROUND

1. Field of Invention

The present invention relates generally to acoustic spectrometry and specifically to the use of acoustic spectrometry to verify the geometry of a cavity within a cast, molded or machined part.

2. Description of Prior Art

A cavity within a cast, molded or machined part often needs to be inspected for defects before additional manufacturing steps add value to a part that may need to be scrapped or reworked. The function of the part may critically depend on the shape and size of the cavity. Positively and quickly identifying defective parts is important in a manufacturing environment. Building assemblies with defective parts may result in shortened product lifetime or poor product performance. Significant prior art has attempted to address this need, however all fall short of solving the problem.

U.S. Pat. No. 1,884,042, Indicator, teaches the use of forcing high-pressure gas through a cavity to be tested and measuring backpressure. Backpressure different from an expected value would result in rejection. While this technique may find major blockages, it is limited to finding blockages that constrict the cavity to a passage smaller than the smallest expected constriction in the cavity and it cannot determine anything at all about blind passages within the cavity. Internal cavities may consist of a complex of interconnecting passages and many defects cannot be detected by this method.

U.S. Pat. No. 2,666,326, Volumetric Measuring Apparatus, teaches a way of detecting volume defects in a cavity by creating a Helmoltz resonator, which measures the volume of the cavity. This technique is good for detecting volume related defects, but will not detect a blockage in a more complicated cavity. Many kinds of shape defects cannot be detected with this apparatus.

U.S. Pat. No. 5,109,699, Sonic Casting Tester, teaches an apparatus and method of blockage detection whereby acoustic wave amplitude attenuation is used to determine a blockage. This technique is again limited to blockages that constrict a passage to a smaller cross section than the smallest cross section expected in the cavity. Shape defects other than blockages of the cavity are not readily detected by this technique.

U.S. Pat. No. 4,480,473, Acoustic Inspection Method, teaches a way of acoustically testing an internal fluid flow path for proper path length, by measuring the phase difference of an acoustic signal traversing the fluid flow path and comparing that to a known good path. Partial blockages may not be detected with this technique, in addition it is not well suited to testing complex cavities that contain blind passages or have multiple paths from input to output.

What is needed is a cavity tester that can test cavity geometry in a more general way and requires little setup.

Objects and Advantages

It is therefore an object of the present invention to provide an apparatus and method for reliably detecting blockages and other geometric anomalies in a cavity within a cast, molded or machined part.

It is a further object of the present invention to provide such an apparatus and method using acoustic techniques.

It is a further object of the present invention to provide such an apparatus and method requiring little or no qualitative decisions that may be completely automated.

It is a further object of the present invention to provide such an apparatus and method that detects defects within blind passages.

It is a further object of the present invention to provide such an apparatus and method that detects missing or incorrectly drilled access holes in such internal cavities.

It is a further object of the present invention to provide such an apparatus and method that does not require a fixture that is inserted into the cavity under test.

It is a further object of the present invention to provide such an apparatus and method that can test multiple unconnected cavities together all at once.

Still other objects and advantages of the present invention will become apparent to those of ordinary skill in the art having reference to the following specification together with its drawings.

SUMMARY

To achieve the foregoing and other objects, according to the main aspect of the present invention, there is provided a method and apparatus for testing the geometry of cavities within a cast, molded or machined part.

In the preferred embodiment of the present invention, the cavity under test is sealed and an acoustic wave is introduced into one end of the cavity. At a second end of the cavity, the amplitude and phase shift of the acoustic wave are measured at a multiplicity of predetermined frequencies. The resulting acoustic spectrum is compared to the spectrum obtained from a known good part.

In another embodiment of the present invention, access holes cast or drilled through the part into the cavity are covered with closed-end tubes. Measuring the acoustic spectrum as in the preferred embodiment now allows the access hole sizes to be compared to those of a reference part along with the geometry of the rest of the cavity.

In another embodiment of the present invention, multiple unconnected cavities in a part are combined into one cavity with a manifold such that the geometry of all cavities may be tested at once.

REFERENCE NUMERALS

Figure 1:
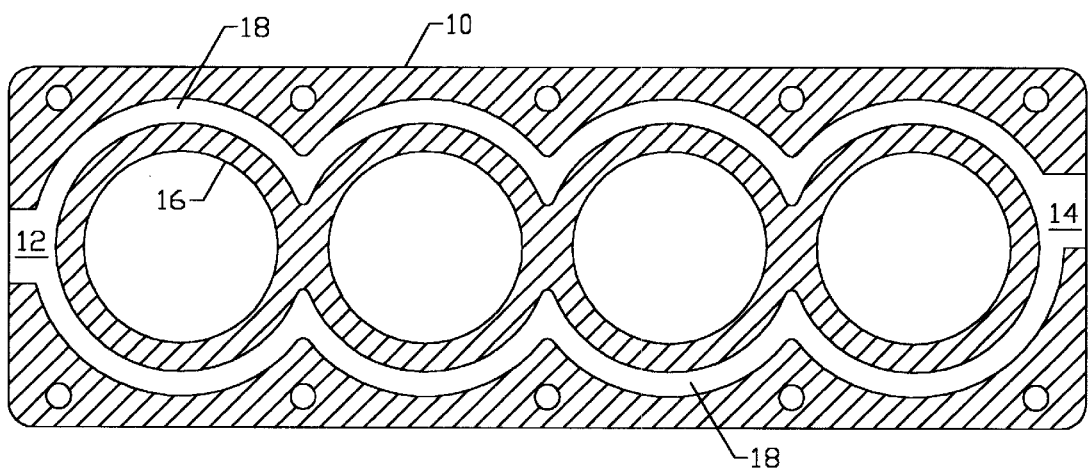
FIG. 1 is a cut-away view of a cylinder block casting with an internal water-cooling passage shown.

10 Cylinder block
12 Inlet port
14 Outlet port
16 Cylinder wall
18 Cooling passage
30 Acoustic transmitter
31 Permanent magnet
32 Coil
33 Insulator and diaphragm support
34 Diaphragm
35 Resilient gasket
36 Stop
37 Pinhole
38 Electrical connection
39 Cavity cover plate
40 Resilient gasket
52 Variable Frequency Generator Block
54 Signal Conditioner Block
56 System Controller Block
58 Spectrum Comparison
61–65 Closed-end Tubes
71 End Seal
72 Manifold
73 Oil drain-back ports
80 Acoustic receiver
81 Acoustic receiver housing
82 Stop
83 Microphone element
84 Resilient gasket
85 Electrical connection
86 Resilient gasket

DESCRIPTION

FIG. 1 is a top sectional view of a 4-cylinder engine block. Adjacent to a portion of each cylinder wall 16, within the cylinder block 10, is a cooling passage or jacket 18. During normal engine operation, a liquid coolant fills the cooling passage 18 and flows from inlet port 12 through the cooling passage to outlet port 14. The coolant carries away excess heat from the cylinder walls. Proper cooling is critical to engine performance and engine life.

The geometry of cooling passage 18 is critical to providing proper cooling of cylinder block 10. Cylinder block 10 may be cast using a lost foam or sand core process in a sand mold. The casting process is prone to a variety of defects including voids and retained sand. Defects in the cooling passage modify the coolant flow through the cooling passage and result in improper cooling.

Figure 2:
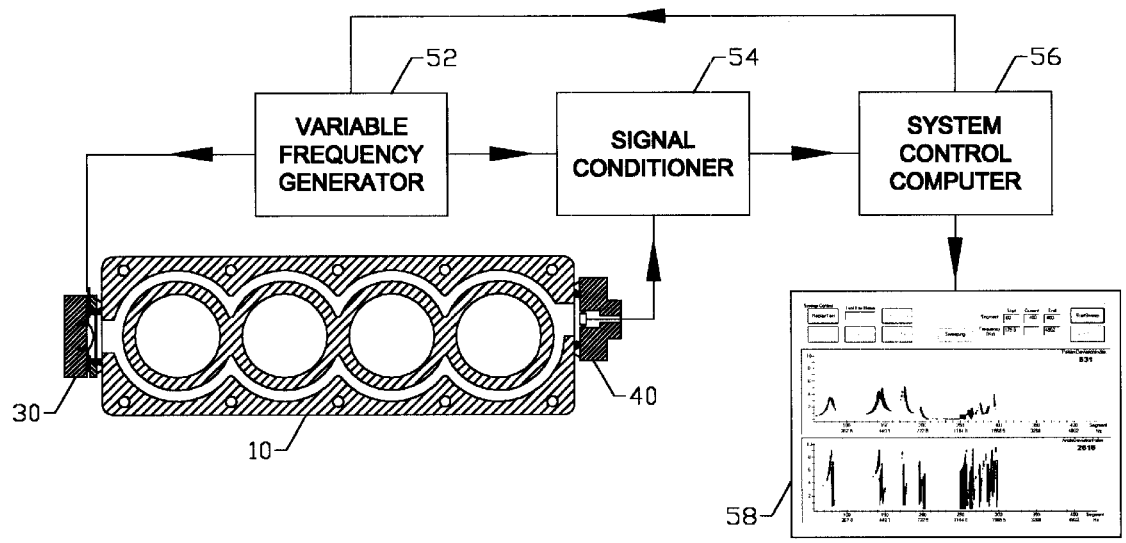
FIG. 2 is a schematic diagram of the system.

In accordance with the present invention, an acoustic spectrometer is used to compare the geometry of a cavity within a part under test to the geometry of the corresponding cavity within a reference part. FIG. 2 shows a schematic diagram of the preferred embodiment of the present invention. Variable frequency generator 52 generates a sine wave that drives acoustic transmitter 30 which drives an acoustic wave into inlet port 12 of cylinder block 10. The acoustic wave is conducted into all parts of the cavity. The amplitude of the acoustic wave at any point in the cavity is the sum of the acoustic wave and its reflections traveling all paths through the cavity to the point. Acoustic receiver 80 positioned at outlet port 14 of cylinder block 10 is responsive to the received acoustic wave and translates the received acoustic wave into a received signal. Signal conditioner 54 acts on the received signal using phase information from variable frequency generator 52 to separate the received signal into in-phase and out-of-phase components using synchronous detection. System control computer 56 digitizes the in-phase and out-of-phase components and calculates signal amplitude and phase at a multiplicity of predetermined frequencies resulting in amplitude and phase acoustic spectrums, the distribution of amplitude or phase measurements ordered by signal frequency. The acoustic spectrum is unique to the geometry of the cavity. The acoustic spectrum of a cavity under test is compared to the acoustic spectrum of a reference cavity to verify the geometry of the cavity under test. In the present embodiment the cavity is the cooling passage 18 of cylinder block 10. The spectrum for the reference cavity may be measured simultaneously with the cavity under test or may be stored from a previous measurement. Block 58 shows a graphic spectrum comparison used to accept or reject the part under test based on spectrum differences between the part under test and the reference part.

Synchronous detection is used in the preferred embodiment because of the high-noise environment for which the preferred embodiment is designed. Synchronous detection is not required to implement the present invention.

Comparison of the cavity under test with the reference cavity may be done on the basis of either the amplitude spectrum, the phase spectrum or both. The preferred embodiment produces difference graphs for both. Characteristics of the two are different. Comparison of phase spectra from two cavities results in a more sensitive comparison as the phase spectrum produces very sharp changes at each resonant frequency. Small changes in the resonant responses of the cavity produce relatively large differences in the spectra relative to amplitude spectrum comparisons. Normal part-to-part variations are also magnified by phase spectrum comparisons. The decision as to which spectrum to use for a particular application depends on the amount of part-to-part variation and the required sensitivity to cavity anomalies.

The same predetermined frequencies are used to form the acoustic spectrum of the cavity under test as those used to form the spectrum of the reference cavity. The size and shape of the features of the cavity create resonances at different frequencies and result in peaks and dips in the acoustic spectrum. The frequency range and the number of predetermined frequencies are determined by the size of the features in the cavity and the size of the anomalies to be detected. Anomalies in the cavity modify the resonances and the resulting acoustic spectrum. The frequency range chosen for a cavity should cover the fundamental resonant frequencies of the cavity. The frequency resolution should be consistent with the feature size of the defects to be detected. Smaller defects require correspondingly finer frequency resolution. The preferred embodiment uses a frequency range of 100 to 5000 Hz at 1% frequency increments, however structures substantially larger or smaller could require test frequencies in the sub-audio or ultrasonic range.

An important aspect of the present invention is sealing the cavity under test. Airtight seals are required on all access holes into the cavity. Seals able to withstand a pressure of 0.1 psi or greater are sufficient. The seal must also be geometrically repeatable from one part measurement to another. The preferred embodiment uses metal plates 39 and 81 with resilient gaskets 40, 84 and 86 to form the seals at the inlet and outlet ports of the cooling passage and positive hard stops to insure geometric repeatability. Geometric repeatability is achieved because the hard stops determine the resulting cavity dimensions, which are not affected by the dimensions of the compressible resilient gasket. The resilient gasket may be a silicone rubber O-ring. It is understood however that other sealing techniques may be used without deviating from the broad principles of the present invention. Mechanical fixturing (not shown) is used to locate the seal assemblies and provide sufficient force to compress the resilient gaskets to the limits of the mechanical stops.

Any additional openings in a cavity under test must be covered by a sealing means that forms an airtight seal with the surface of the part.

Figure 3A:
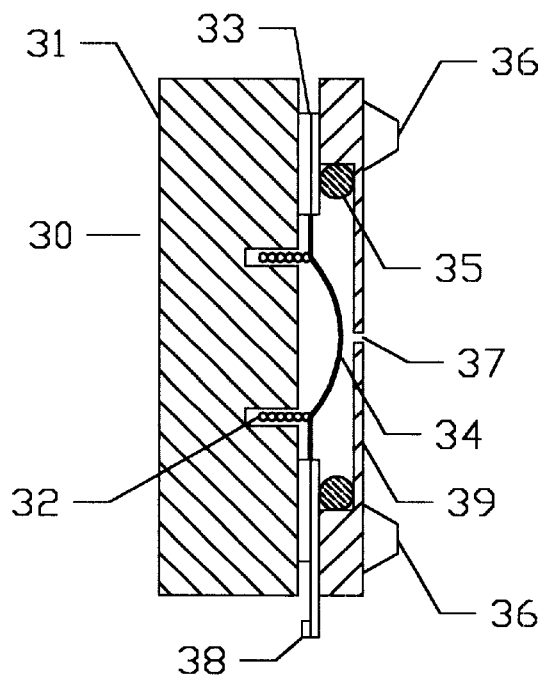
FIG. 3a shows details of the acoustic transmitter.
Figure 3B:
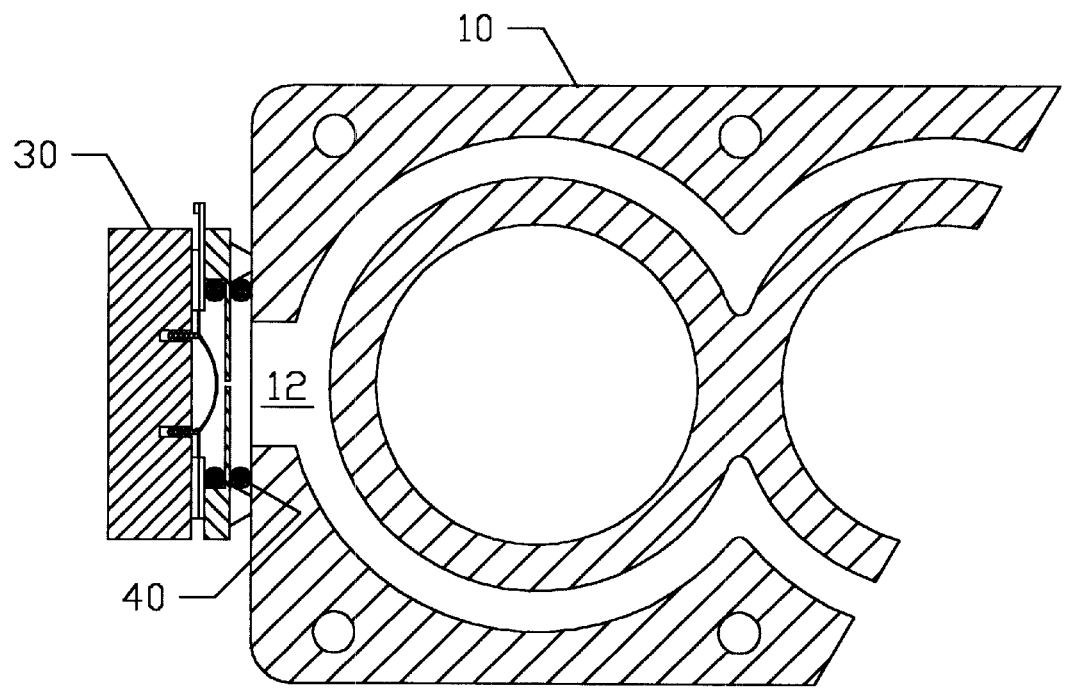
FIG. 3b shows the connection of the acoustic transmitter to the cylinder block.

FIGS. 3a and 3b show details of the acoustic transmitter 30 used in the preferred embodiment. The acoustic transmitter 30 consists of a speaker driving a pinhole 37 in metal plate 39 sealing the inlet port. The speaker consists of coil 32 in the field of permanent magnet 31 driving diaphragm 34. The diaphragm is held in place by insulator 33. Resilient gasket 35 provides an airtight seal between plate 39 and insulator 33. Stops 36 provides a hard stop for the compression of resilient gasket 40 when acoustic transmitter 30 is clamped in position on cylinder block 10. The seal mechanism, including the mechanical fixturing, positions the pinhole relative to the inlet port such that the pinhole is in the same position relative to the inlet port for the cavity under test as it was on the reference part. The size of the pinhole and the acoustic output power of the speaker must be the same for measurements of the cavity under test and the reference cavity. The acoustic transmitter 30, used in the preferred embodiment, consisting of a speaker driving a pinhole, increased the sharpness of cavity resonances as compared to a speaker directly driving the cavity. The size of the pinhole in the preferred embodiment is 0.081 inches.

Acoustic transmitter 30 must provide a generally linear response over the frequency range of interest. The acoustic transmitter must provide repeatable conversion efficiency so that with the same signal power input, the same acoustic power output will be achieved. The acoustic transmitter must be placed at the same position relative to the cavity in the cavity under test, as in the reference cavity.

The preferred embodiment uses a moving coil audio speaker driver to produce the acoustic wave, however other acoustic devices could be used such as a piezo electric device or a moving piston device, without deviating from the broad outline of the present invention. The requirements of the acoustic transmitter means are the ability to convert a signal from the variable frequency generator into an acoustic wave over the frequency range of interest. Operation beyond the audio range requires an acoustic speaker driver that covers the frequency range of interest.

Figure 4A:
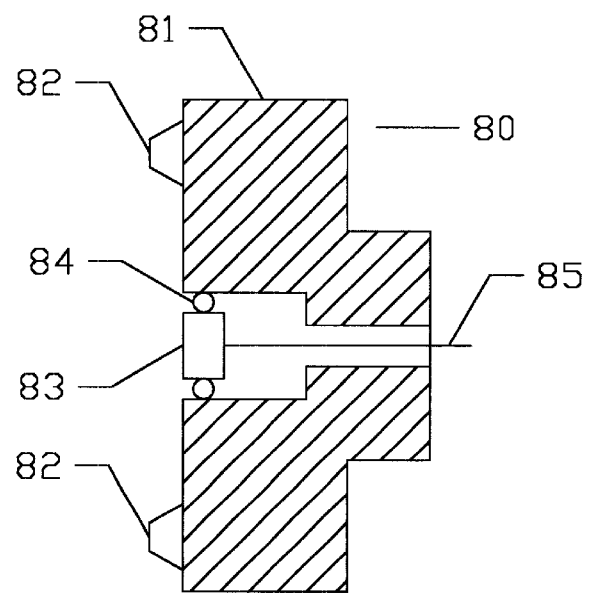
FIG. 4a shows details of the acoustic receiver.
Figure 4B:
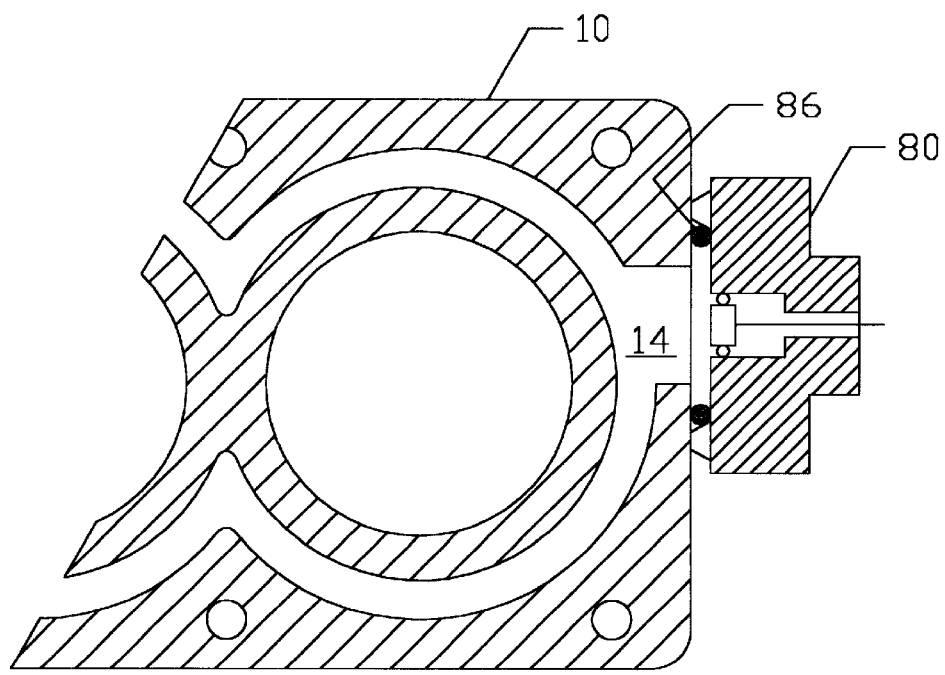
FIG. 4b shows the connection of the acoustic receiver to the cylinder block.

FIGS. 4a and 4b show details of acoustic receiver 80 used the preferred embodiment. Acoustic receiver 80 consists of a housing 81 with stops 82 and microphone element 83. Microphone element 83 is attached to housing 81 with resilient gasket 84, which produces an airtight seal. The electrical connection to microphone element 83 is via connection wires 85. In the preferred embodiment, acoustic receiver 80 is a part of the outlet port seal assembly. Stops 82 provide hard stops to limit compression of resilient gasket 86 when acoustic receiver 80 is clamped in position on cylinder block 10. The outlet port seal, including the mechanical fixturing, positions acoustic receiver 80 relative to the outlet port such that the acoustic receiver is in the same position relative to the outlet port for the cavity under test as for the reference cavity. Exact placement of acoustic transmitter 30 and acoustic receiver 80 in relation to the cavity is not critical, however, in order to compare two cavities, the acoustic transmitter and acoustic receiver must be in the same corresponding positions relative to the two cavities.

Figure 5:
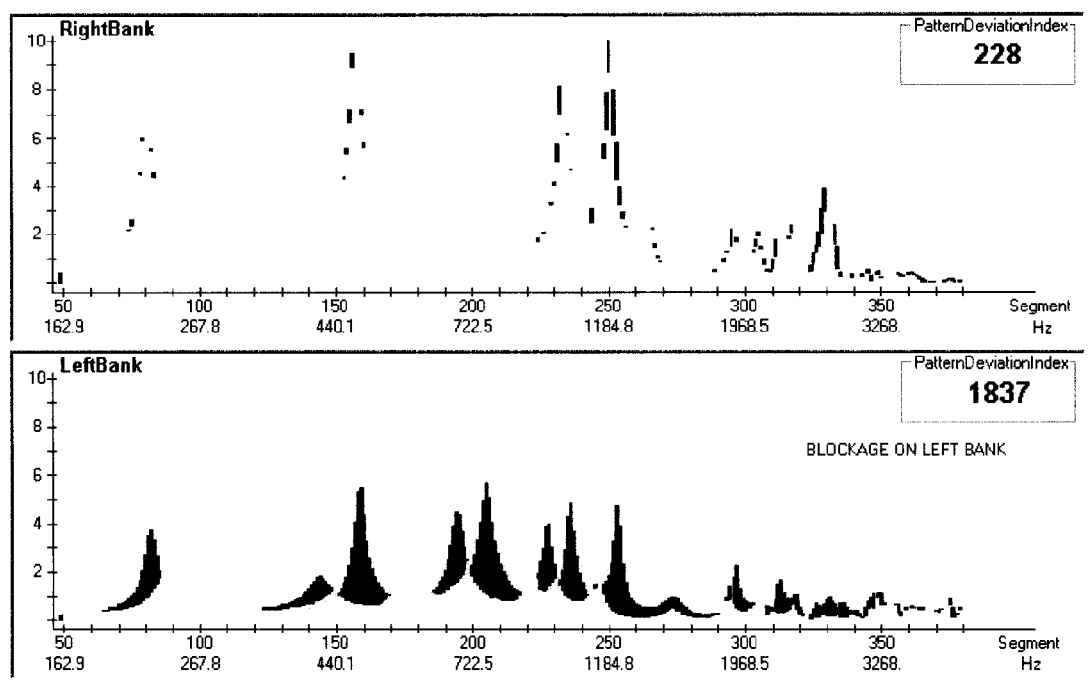
FIG. 5 shows graphs comparing the amplitude of the acoustic spectrum of two cavities under test to that of two reference cavities.

FIG. 5 shows a comparison of the amplitude spectrum of two cavities under test with that of their respective reference cavities. Spectrums of the reference cavities are shown in gray. Differences between the cavity under test and the reference cavity are shown in black. The top graph shows a cavity that is essentially the same as the reference cavity. The bottom graph shows a cavity with a significant geometric difference from the reference cavity.

Peaks in the amplitude acoustic spectrum are associated with resonances in the response of the cavity to the transmitted acoustic wave. The shape of the acoustic spectrum is unique to the geometry of the cavity. Changes in the geometry of a cavity change the shape of the measured spectrum. A geometric anomaly in the cavity can change the position or amplitude of one or more of the peaks in the amplitude response depending on its size and position in the cavity. The differences in the spectra are highlighted in black to allow an operator to make a quick determination of the differences between the spectra. Color may also be used to highlight the differences. In the preferred embodiment, a 20% deviation in amplitude is allowed to accommodate normal part variations. Outside of this 20% acceptance range, the difference between the reference spectrum and the spectrum from the part under test are shown in black. The operator can see the deviation of the two patterns at a glance.

An automatic comparison method may be used to accept or reject a part based on the magnitude of differences between the spectra. An automated decision on the suitability of a part may be made based on differences in the spectra between the cavity under test and the reference cavity. In the preferred embodiment, a Pattern Deviation Index is calculated which is the sum of the amplitude differences between the reference spectrum and the spectrum of the part under test.

Figure 6:
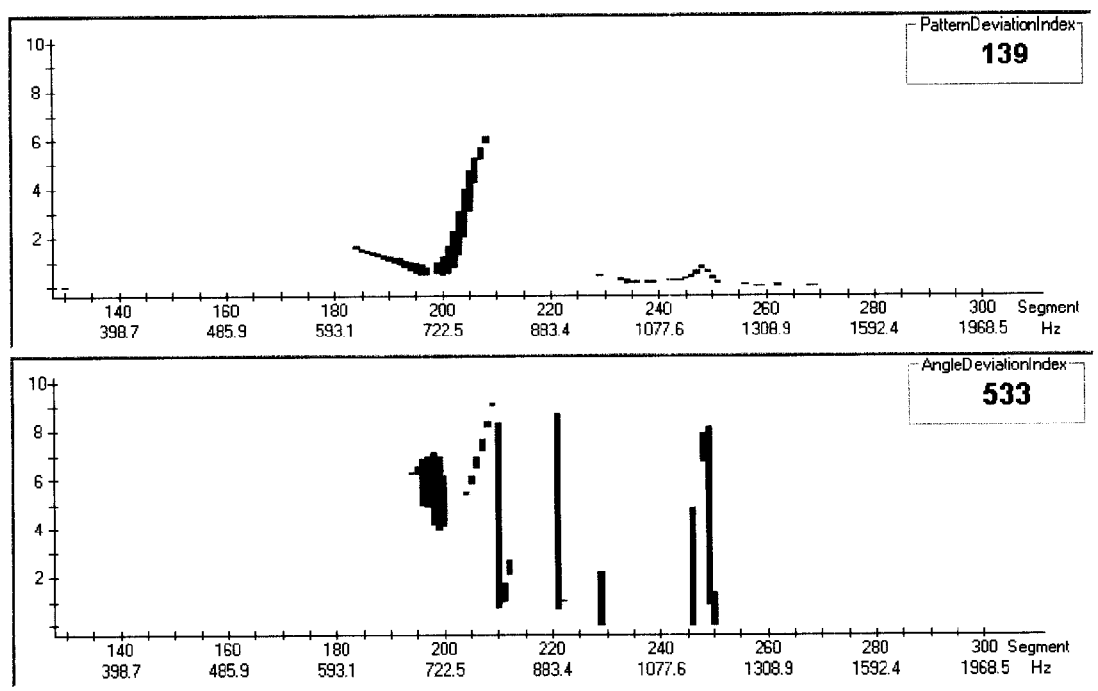
FIG. 6 shows graphs comparing the amplitude and phase of the acoustic spectrum of a cavity under test to a reference cavity.

FIG. 6 shows graphs of the amplitude spectrum, top graph, and phase spectrum, bottom graph, of the same cavity against a reference cavity. The response of the reference cavity is shown in gray. Differences between the cavity under test and the reference cavity are highlighted in black. Peaks in the amplitude spectrum are associated with phase changes in the phase spectrum.

Figure 7:
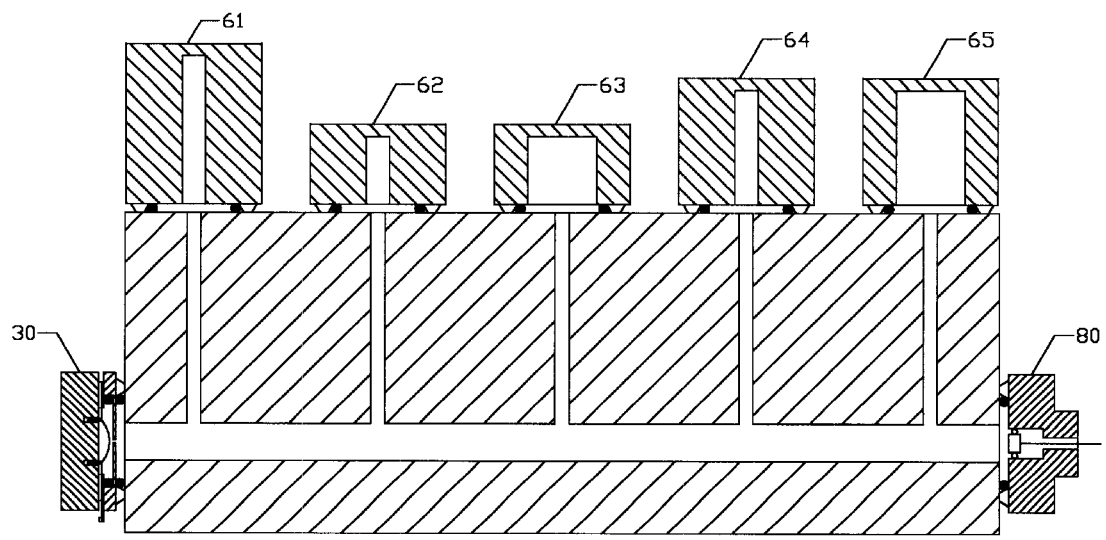
FIG. 7 shows a casting with cavity access holes sealed by closed-end tubes.

FIG. 7 shows another embodiment of the present invention. A cavity within a part has one or more access holes drilled into the cavity. The cavity is tested in the same manner as in the previous embodiment, by sealing the cavity and measuring the acoustic spectrum of the cavity. The holes into the cavity are sealed with closed-end tubes. The closed-end tubes introduce additional resonances within the cavity, which show up in the acoustic spectrum, allowing the sizes of the holes to be compared with corresponding holes in the reference cavity. The resonant frequency of a hole and a closed-end tube is dependent on the area of the hole and the volume of the closed-end tube. Sealing the corresponding holes into the cavity under test and the reference cavity with the same sized closed-end tube allows the acoustic spectrum to compare the hole sizes between the cavity under test and the reference cavity. In a cavity with multiple holes that need to be compared, the volume of the closed-end tubes associated with each hole may be adjusted such that the resonances fall at different frequencies, thereby allowing multiple holes of the same size to be compared without overlap in the frequency spectrum. This approach can also be used to enhance the response to a particular geometric anomaly, or to separate spectrum pattern components overlaying each other from different cavity paths. As shown, the closed-end tubes 61-65 include stops that limit the compression of the resilient gaskets between the closed-end tubes and the part under test.

Figure 8:
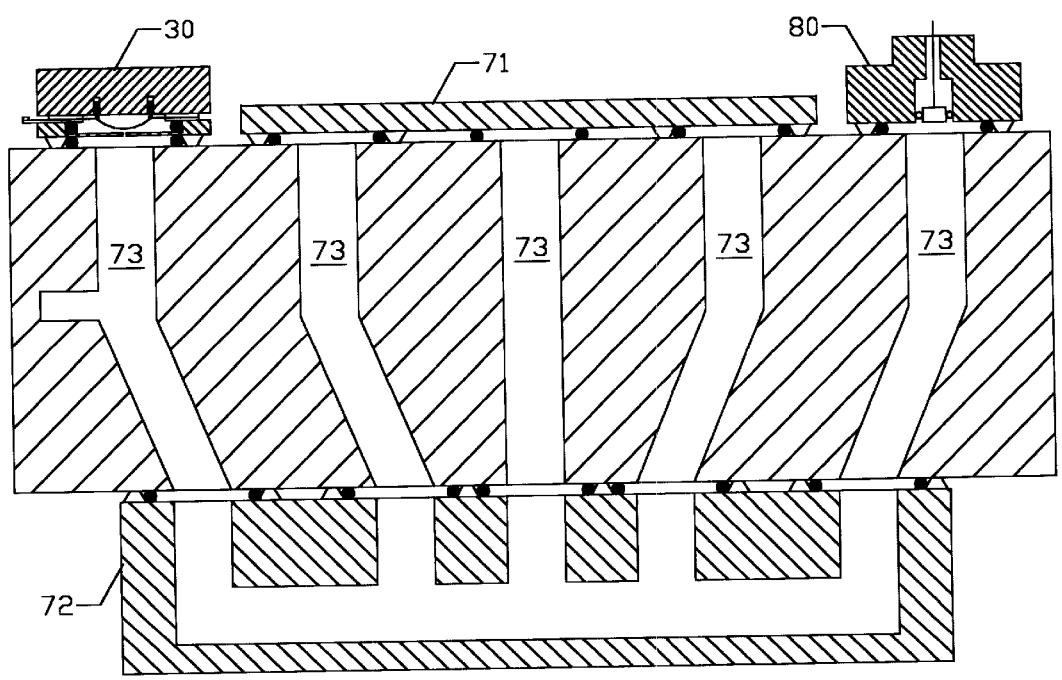
FIG. 8 shows a manifold combining multiple cavities into one cavity. numerals

In another embodiment of the present invention shown in FIG. 8, a group of internal cavities are combined into a single cavity by a manifold. Oil drain-back ports 73 are combined into one cavity by manifold 72 and a seal 71. In this embodiment acoustic transmitter 30 and acoustic receiver 80 are mounted on the ends of two different oil drain-back ports. The manifold forms a seal with the part such that the manifold and the five drain-back ports form a sealed system. Resilient gaskets and stops mounted on the manifold seal the ends of the oil drain-back ports, much as with the closed-end tubes. The formed larger cavity is then tested as in the preferred embodiment. An acoustic spectrum is measured and compared to the acoustic spectrum of a reference cavity.

What is claimed is:

1. An acoustic spectrometer for testing the geometry of a cavity within a cast, molded or machined part, said cavity having openings at two ends, comprising:
    a) airtight seals covering said openings in said cavity;
    b) an acoustic transmitter means in acoustic communication with a first end of said cavity, said acoustic transmitter transmitting an acoustic wave into said cavity;
    c) an acoustic receiver at a second end of said cavity, in acoustic communication with said cavity for receiving said acoustic wave conducted through said cavity and producing a received signal responsive to said acoustic wave;
    d) a variable frequency generator operatively connected to said acoustic transmitter whereby a generated signal is transformed into an acoustic wave by said acoustic transmitter;
    e) an amplitude detector responsive to said received signal producing an amplitude signal;
    f) a control means controlling the frequency of said variable frequency generator to a multiplicity of predetermined frequencies, said control means also responsive to said amplitude signal, producing an acoustic amplitude spectrum; and
    g) a means to compare said acoustic amplitude spectrum with an acoustic amplitude spectrum produced from a corresponding cavity in a similar part having known properties as reference spectrum.

2. The acoustic spectrometer of claim 1, said acoustic transmitter means comprising an acoustic speaker driver transmitting an acoustic wave into said cavity through a pinhole.

3. The acoustic spectrometer of claim 1, said cavity additionally having one or more holes through said part, connecting said cavity with a surface of said part, further comprising:
    a) a closed-end tube covering each of said holes; and
    b) each closed-end tube forming an airtight seal with the surface of said part.

4. The acoustic spectrometer of claim 3, said acoustic transmitter means comprising an acoustic speaker driver transmitting an acoustic wave into said cavity through a pinhole.

5. The acoustic spectrometer of claim 1, said part further comprising multiple unconnected cavities, said cavities each having at least one opening in a surface of said part, further comprising:
    a) a manifold joining said unconnected cavities into a single cavity by covering at least one opening of each of said unconnected cavities, said manifold forming an airtight seal over each of said openings; and
    b) a sealing means disposed over any uncovered ends of said cavities, said sealing means forming an airtight seal with the surface of said part.

6. The acoustic spectrometer of claim 5, said acoustic transmitter means comprising an acoustic speaker driver transmitting an acoustic wave into said cavity through a pinhole.

7. An acoustic spectrometer for testing the geometry of a cavity within a cast, molded or machined part, said cavity having openings at two ends, comprising:
    a) airtight seals covering said openings in said cavity;
    b) an acoustic transmitter means in acoustic communication with a first end of said cavity, said acoustic transmitter transmitting an acoustic wave into said cavity;
    c) an acoustic receiver at a second end of said cavity, in acoustic communication with said cavity for receiving said acoustic wave conducted through said cavity and producing a received signal responsive to said acoustic wave;
    d) a variable frequency generator operatively connected to said acoustic transmitter whereby a generated signal is transformed into an acoustic wave by said acoustic transmitter;
    e) a phase detector responsive to said received signal and said variable frequency generator producing a phase signal;
    f) a control means controlling the frequency of said variable frequency generator to a multiplicity of predetermined frequencies, said control means also responsive to said phase signal, producing an acoustic phase spectrum; and
    g) a means to compare said acoustic phase spectrum with an acoustic phase spectrum produced from a corresponding cavity in a similar part having known properties as reference spectrum.

8. The acoustic spectrometer of claim 7, said acoustic transmitter means comprising an acoustic speaker driver transmitting an acoustic wave into said cavity through a pinhole.

9. The acoustic spectrometer of claim 7, said cavity additionally having one or more holes through said part, connecting said cavity with a surface of said part, further comprising:
    a) a closed-end tube covering each of said holes; and
    b) each closed-end tube forming an airtight seal with the surface of said part.

10. The acoustic spectrometer of claim 9, said acoustic transmitter means comprising an acoustic speaker driver transmitting an acoustic wave into said cavity through a pinhole.

11. The acoustic spectrometer of claim 7, said part further comprising multiple unconnected cavities, said cavities each having at least one opening in a surface of said part, further comprising:
    a) a manifold joining said unconnected cavities into a single cavity by covering at least one opening of each of said unconnected cavities, said manifold forming an airtight seal over each of said openings; and
    b) a sealing means disposed over any uncovered ends of said cavities, said sealing means forming an airtight seal with the surface of said part.

12. The acoustic spectrometer of claim 11, said acoustic transmitter means comprising an acoustic speaker driver transmitting an acoustic wave into said cavity through a pinhole.

13. A method for testing the geometry of a cavity within a cast, molded or machined part, said cavity having openings at two ends, whereby the acoustic spectrum of acoustic waves conducted through the cavity to be tested are compared with the acoustic spectrum of a corresponding cavity in a similar part having known properties as reference spectrum, comprising:

a) installing airtight seals over the openings of said cavity;

b) introducing an acoustic wave of constant amplitude and frequency into a first end of said cavity;

c) said acoustic wave being conducted throughout the cavity;

d) receiving said acoustic wave at a second end of said cavity and converting said acoustic wave into a received signal;

e) detecting the amplitude of said received signal; and f) performing steps b through e at a multiplicity of predetermined frequencies to form an acoustic spectrum.

14. The method for testing the geometry of a cavity of claim 13, said cavity additionally having one or more holes through said part, connecting said cavity with a surface of said part, further comprising, a) covering said holes with closed-end tubes, said closed-end tubes forming an airtight seal with said surface of said part.

15. The method for testing the geometry of a cavity of claim 13, said part further comprising multiple unconnected cavities, said cavities each having at least one opening in a surface of said part, further comprising:

a) joining said unconnected cavities into a single cavity by covering at least one opening of each of said unconnected cavities with a manifold, said manifold forming an airtight seal with said surface of said part; and b) sealing any uncovered ends of said cavities with a sealing means, said sealing means forming an airtight seal with said surface of said part.

16. A method for testing the geometry of a cavity within a cast, molded or machined part, said cavity having openings at two ends, whereby the acoustic spectrum of acoustic waves conducted through the cavity to be tested are compared with the acoustic spectrum of a corresponding cavity in a similar part having known properties as reference spectrum, comprising:

a) installing airtight seals over the openings of said cavity;

b) introducing an acoustic wave of constant amplitude and frequency into a first end of said cavity;

c) said acoustic wave being conducted throughout the cavity;

d) receiving said acoustic wave at a second end of said cavity and converting said acoustic wave into a received signal;

e) detecting the phase difference between said received signal and said acoustic wave at said first end of said cavity; and f) performing steps b through e at a multiplicity of predetermined frequencies to form an acoustic spectrum.

17. The method for testing the geometry of a cavity of claim 16, said cavity additionally having one or more holes through said part, connecting said cavity with a surface of said part, further comprising, a) covering said holes with closed-end tubes, said closed-end tubes forming an airtight seal with said surface of said part.

18. The method for testing the geometry of a cavity of claim 16, said part further comprising multiple unconnected cavities, said cavities each having at least one opening in a surface of said part, further comprising:

a) joining said unconnected cavities into a single cavity by covering at least one opening of each of said unconnected cavities with a manifold, said manifold forming an airtight seal over each of said openings; and b) sealing any uncovered ends of said cavities with a sealing means, said sealing means forming an airtight seal with the surface of said part.

\* \* \* \* \*